United States Patent
Buckton et al.

(10) Patent No.: US 9,668,716 B2
(45) Date of Patent: Jun. 6, 2017

(54) ULTRASOUND IMAGING SYSTEM AND METHOD FOR ULTRASOUND IMAGING A THREE DIMENSIONAL VOLUME

(75) Inventors: Daniel Buckton, Zipf (AT); Christian Perrey, Zipf (AT)

(73) Assignee: General Electric Company, Schenectady, NY (US)

(*) Notice: Subject to any disclaimer, the term of this patent is extended or adjusted under 35 U.S.C. 154(b) by 1367 days.

(21) Appl. No.: 12/965,179

(22) Filed: Dec. 10, 2010

(65) Prior Publication Data
US 2012/0150036 A1    Jun. 14, 2012

(51) Int. Cl.
| | | |
|---|---|---|
| *A61B 8/00* | (2006.01) | |
| *A61B 8/08* | (2006.01) | |
| *A61B 8/14* | (2006.01) | |
| *G01S 7/52* | (2006.01) | |
| *G03B 42/06* | (2006.01) | |
| *G01S 15/89* | (2006.01) | |

(52) U.S. Cl.
CPC ............ *A61B 8/5207* (2013.01); *A61B 8/145* (2013.01); *A61B 8/466* (2013.01); *A61B 8/483* (2013.01); *A61B 8/5246* (2013.01); *A61B 8/5253* (2013.01); *A61B 8/5284* (2013.01); *G01S 7/52087* (2013.01); *G03B 42/06* (2013.01); *G01S 15/8993* (2013.01)

(58) Field of Classification Search
CPC ......... A61B 8/145; A61B 8/466; A61B 8/483; A61B 8/5207; A61B 8/5253; A61B 8/5284; A61B 8/5246; G03B 42/06; G01S 14/8993; G01S 7/52087
See application file for complete search history.

(56) References Cited

U.S. PATENT DOCUMENTS

| | | |
|---|---|---|
| 6,638,225 B2 | 10/2003 | Kamiyama |
| 6,966,878 B2 | 11/2005 | Schoisswohl et al. |
| 6,980,844 B2 | 12/2005 | Schoisswohl |
| 7,175,598 B2 | 2/2007 | Yoneyama |

(Continued)

FOREIGN PATENT DOCUMENTS

| | | |
|---|---|---|
| CN | 101080202 A | 11/2007 |
| CN | 101331406 A | 12/2008 |

OTHER PUBLICATIONS

Yao Wang. "Ultrasound Imaging" EL5823/BE6203—Medical Imaging—I. Polytechnic University, Brooklyn, NY 11201.*

(Continued)

*Primary Examiner* — Amanda Lauritzen Moher
(74) *Attorney, Agent, or Firm* — Dean D. Small; The Small Patent Law Group, LLC

(57) ABSTRACT

A method of ultrasound imaging includes acquiring plural groups of ultrasound data sets in an imaged volume that at least partially encompasses an object. The groups of ultrasound data sets include ultrasound image data obtained by transmitting one or more ultrasound pulses from one or more transducer elements into different zones of the imaged volume. The method also includes arranging the ultrasound data sets into one or more temporal groups based on when the ultrasound data sets are acquired. The ultrasound data sets in each temporal group are acquired during a common time period. The method further includes constructing a three-dimensional image of the object based on the ultrasound data sets in at least one of the temporal groups.

19 Claims, 8 Drawing Sheets

(56) References Cited

U.S. PATENT DOCUMENTS

| | | |
|---|---|---|
| 7,454,048 B2 | 11/2008 | Schoisswohl et al. |
| 2003/0097068 A1* | 5/2003 | Hossack et al. .............. 600/443 |
| 2006/0078196 A1* | 4/2006 | Sumanaweera et al. ..... 382/154 |
| 2008/0267479 A1 | 10/2008 | Jago |
| 2008/0300486 A1 | 12/2008 | Tirumalai et al. |
| 2009/0054776 A1* | 2/2009 | Sasaki .................... A61B 8/543 600/443 |
| 2009/0112093 A1* | 4/2009 | Bae et al. ..................... 600/447 |
| 2009/0182234 A1 | 7/2009 | Perrey et al. |
| 2010/0036247 A1 | 2/2010 | Yamamoto et al. |
| 2010/0174191 A1* | 7/2010 | Lin ................... A61B 5/02007 600/443 |
| 2010/0185088 A1 | 7/2010 | Perrey et al. |

OTHER PUBLICATIONS

Unofficial English Translation of Chinese Office Action and Search Report issued in connection with corresponding CN Application No. 201110429375.6 on Oct. 31, 2014.

\* cited by examiner

ULTRASOUND IMAGING SYSTEM AND METHOD FOR ULTRASOUND IMAGING A THREE DIMENSIONAL VOLUME

BACKGROUND OF THE INVENTION

The subject matter described herein relates to ultrasound imaging systems and methods.

Some known ultrasound imaging systems are used to acquire three-dimensional images of a periodically moving body, such as a beating heart. These systems may employ spatio-temporal image correlation (STIC) to generate a set of three-dimensional images at various phases of the periodic movement of the heart. In order to acquire sufficient image data to create the three-dimensional images, the transducer elements in an ultrasound probe are slowly mechanically steered across the heart. For example, the transducer elements may be mechanically swept across the heart such that many ultrasound pulses are transmitted toward the heart at various elevational angles and resulting echoes of the pulses off of the body are received. Ultrasound image data is generated based on the received echoes.

The transducer elements can be slowly swept over a range of elevational angles (such as 0 degrees to 20 degrees) while the ultrasound image data is acquired at a relatively fast frame rate. As a result, a considerable amount of ultrasound image data is acquired. The fast frame rate permits the systems to acquire ultrasound image data during the several phases of the periodic motion of the heart. The ultrasound image data is reconstructed into the three-dimensional images based on when and where the ultrasound image data was acquired. For example, the ultrasound image data that is acquired during a common phase of the periodic motion of the heart at different spatial locations may be combined into a three-dimensional image.

However, with some relatively fast moving bodies, such as fetal hearts, image artifacts may be generated in the three-dimensional images. For example, a fetus in a mother's womb may move around, thereby making it difficult to obtain spatially consistent ultrasound image data during one or more of the phases of the periodic motion of the heart. The position of the heart may change relatively rapidly during the sweep of the transducer elements across the heart and cause spatially inconsistent or incoherent ultrasound image data to be acquired during a common phase of the periodic motion of the heart.

A need exists for improving the acquisition of ultrasound image data of periodically moving bodies to generate one or more ultrasound images.

BRIEF DESCRIPTION OF THE INVENTION

In one embodiment, a method of ultrasound imaging is provided. The method includes acquiring plural groups of ultrasound data sets in an imaged volume that at least partially encompasses an object. The groups of ultrasound data sets include ultrasound image data obtained by transmitting one or more ultrasound pulses from one or more transducer elements into different zones of the imaged volume. The method also includes arranging the ultrasound data sets into one or more temporal groups based on when the ultrasound data sets are acquired. The ultrasound data sets in each temporal group are acquired during a common time period. The method further includes constructing a three-dimensional image of the object based on the ultrasound data sets in at least one of the temporal groups. In one aspect, the method also includes acquiring the ultrasound data sets of a periodically moving body and arranging the ultrasound data sets includes arranging the ultrasound data sets into the temporal groups associated with different phases of periodic motion of the body.

In another embodiment, an ultrasound imaging system is provided. The ultrasound system includes an ultrasound probe, a beamforming module, a timing module, and a spatial and temporal image correlation (STIC) module. The ultrasound probe includes transducer elements that are configured to emit ultrasound pulses into an imaged volume that includes a body and to receive ultrasound echoes reflected off of the body. The beamforming module is communicatively coupled with the ultrasound probe and is configured to steer one or more of the ultrasound pulses to acquire plural groups of ultrasound data sets with the groups of ultrasound data sets from different zones of the imaged volume. The timing module is communicatively coupled with the beamforming module to receive the ultrasound data sets. The timing module associates the ultrasound data sets with different temporal groups based on when the ultrasound data sets are acquired. The STIC module is communicatively coupled with the timing module to receive the temporal groups of the ultrasound data sets. The STIC module is configured to construct a three-dimensional image of the object based on the ultrasound data sets in at least one of the temporal groups. In one aspect, the imaged volume includes plural zones separated by a dividing plane and the beamforming module is configured to sequentially acquire the ultrasound data sets in each of the groups on opposite sides of the dividing plane.

In another embodiment, a computer readable storage medium for an ultrasound imaging system having a processor is provided. The medium includes one or more sets of instructions stored thereon for directing the processor to acquire plural groups of ultrasound data sets in an imaged volume that at least partially encompasses a periodically moving object. The groups of ultrasound data sets include data obtained from different zones of the imaged volume. The instructions also direct the processor to arrange the ultrasound data sets into one or more temporal groups based on when the ultrasound data sets are acquired. The ultrasound data sets in each temporal group are acquired during a common time period. The instructions also direct the processor to construct a three-dimensional image of the object based on the ultrasound data sets in at least one of the temporal groups.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION OF THE INVENTION

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Unless explicitly stated to the contrary, embodiments "comprising," "including," or "having" an element or a plurality of elements having a particular property may include additional such elements not having that property.

The subject matter described herein relates to ultrasound imaging systems and methods for ultrasound imaging three-dimensional volumes. One or more embodiments described herein may be used to acquire several three-dimensional images of a periodically moving body, such as a fetal heart, at various temporal phases of the periodic motion of the body. The systems and methods may acquire sets of ultrasound data, such as two-dimensional image planes, in a relatively rapid fashion by obtaining groups of the ultrasound data sets in near simultaneous fashion from different zones of an imaged volume that includes the body. The ultrasound data sets are organized into temporal groups based on when the image planes were obtained. The ultrasound data sets in each temporal group may be spatially stitched together, interleaved, or otherwise combined to form a different three-dimensional image of the body at different temporal phases of the moving body.

Figure 1:
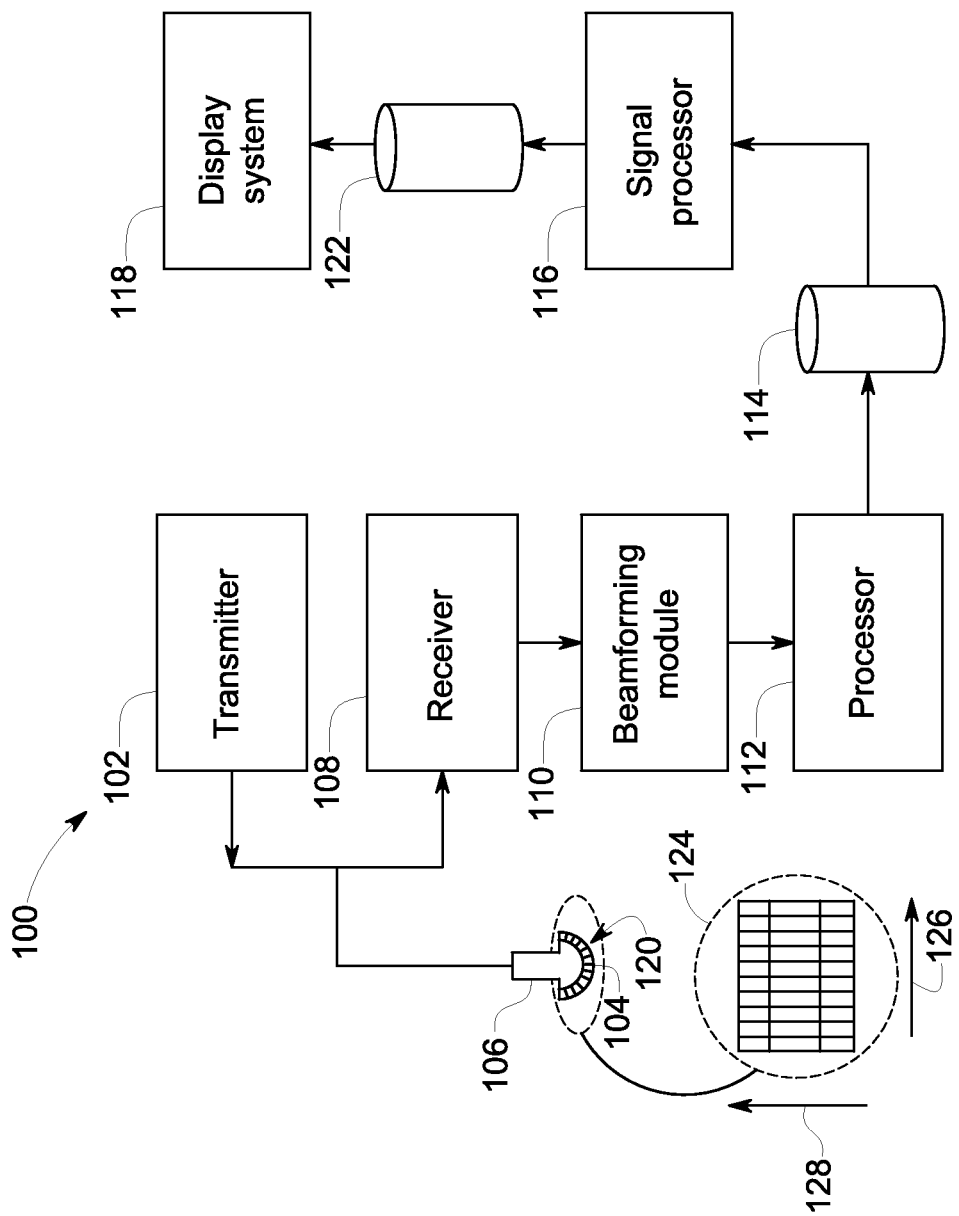
FIG. 1 is a block diagram of one embodiment of an ultrasound system.

FIG. 1 is a block diagram of one embodiment of an ultrasound system 100. The ultrasound system 100 includes a transmitter 102 that is controlled by a beamforming module 110. The beamforming module 110 causes the transducer 102 to drive an array 120 of transducer elements 104 of an ultrasound probe 106. The beamforming module 110 controls transmission of ultrasound pulses that are emitted by the transducer elements 104, such as the timing at which the pulses are emitted and the direction in which the pulses are emitted. In one embodiment, the array 120 is a two-dimensional array of transducer elements 104. As shown in the detail view 124, the array 120 may include plural transducer elements 104 disposed side-by-side or adjacent to each other along first and second orthogonal directions 126, 128. The transducer elements 104 emit pulsed ultrasonic signals into an image volume that at least partially encompasses an object to be imaged. While a curved geometry of the transducer elements 104 is shown, one or more other geometries can be used. At least some of the ultrasonic signals transmitted by the transducer elements 104 may be back-scattered from structures in the object to produce echoes of varying intensity that are received by the transducer elements 104.

The echoes are received by the transducer elements 104 and electric signals are generated by one or more of the transducer elements 104 based on the varying intensity. The electric signals are communicated to a receiver 108 that is controlled by the beamforming module 110. The beamforming module 110 performs beamforming processes on the signals to form beamformed radio frequency (RF) signals that represent acquired ultrasound image data. For example, the beamforming module 110 may spatially combine the ultrasound data acquired by individual transducer elements 104 into ultrasound images.

In one embodiment, the beamforming module 110 represents one or more sets of instructions, such as software applications, stored on a tangible and non-transitory computer readable storage medium, such as a computer hard drive, RAM, ROM, EEPROM, flash memory, and the like. The beamforming module 110 electrically steers the ultrasound pulses emitted by the transducer elements 104 (or a subset of the transducer elements 104) along one or more directions or image planes. By "electrically steer," it is meant that the beamforming module 110 directs the transducer elements 104 to transmit ultrasound signals in various directions without moving the transducer elements 104 or probe 106 relative to the object that is imaged by the ultrasound system 100. Alternatively, the beamforming module 110 may direct the transducer elements 104 to be mechanically steered relative to the object being imaged. For example, the beamforming module 110 may direct one or more motors or other actuators to move the transducer elements 104 and/or probe 106 relative to the object being imaged in order to transmit ultrasound signals along different directions and/or image planes.

The ultrasound image data that is acquired along different directions and/or image planes is communicated to a processor 112. In another embodiment, the processor 112 may include a complex demodulator that demodulates the RF signal to form IQ data pairs that represent the acquired ultrasound image data. The acquired ultrasound image data may be routed to an RF/IQ memory buffer 114 for temporary or longer-term storage and/or retrieval.

The ultrasound system 100 also includes a signal processor 116 to process the acquired ultrasound image data and prepare image planes for visual presentation to one or more operators on a display system 118. An image buffer 122 can be provided for storing processed image planes of acquired ultrasound image data that are not displayed immediately. The image buffer 122 may be embodied in a tangible and non-transitory computer readable storage medium such as a computer hard drive, flash drive, RAM, ROM, EEPROM, and the like.

In one embodiment, the signal processor 116 performs one or more processing operations on the acquired ultrasound image data. Acquired ultrasound image data may be processed in real-time during a scanning session as the echo signals are received. Additionally or alternatively, the ultrasound image data may be stored temporarily in the buffer 114 during a scanning session and processed in less than real-time in a live or off-line operation.

Figure 2:
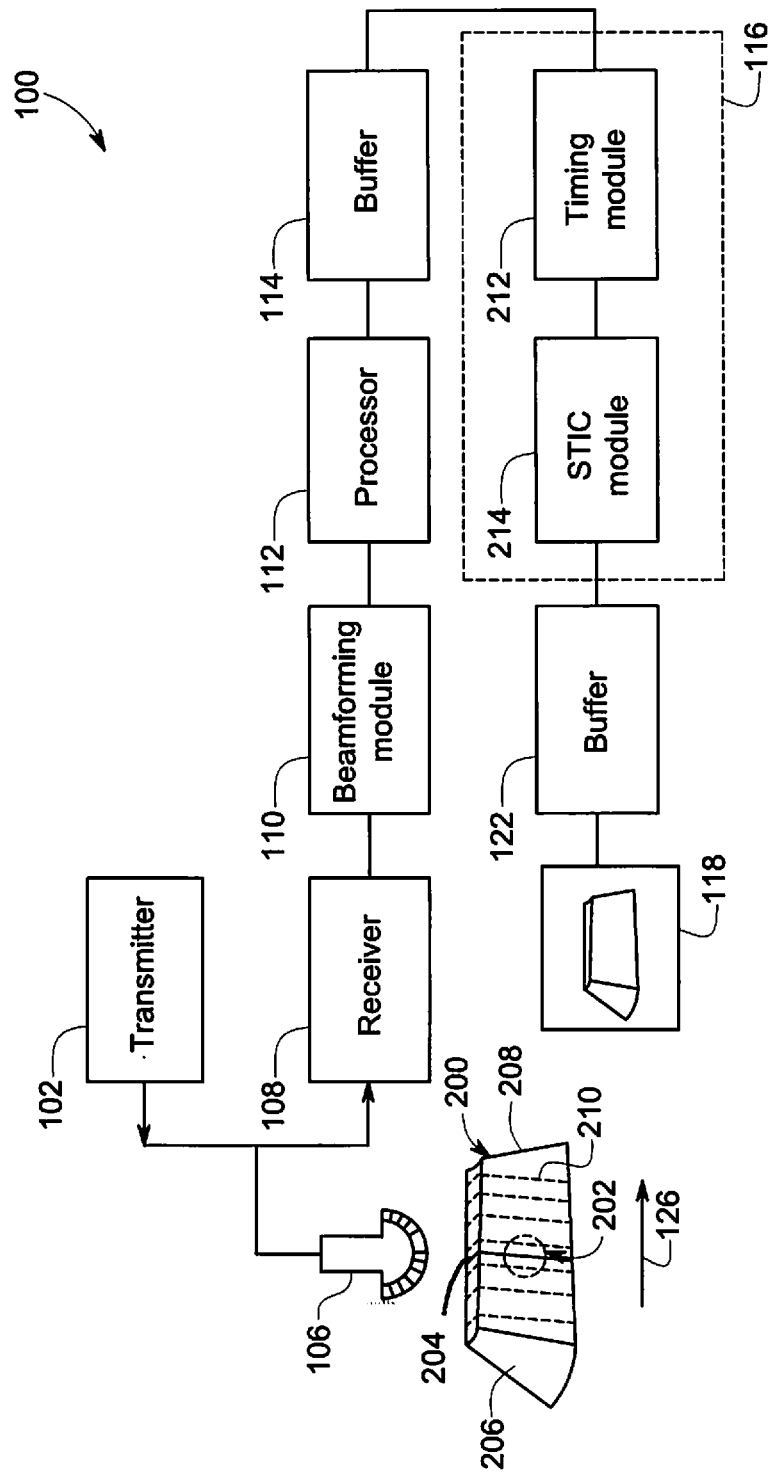
FIG. 2 is another block diagram of the ultrasound system shown in FIG. 1 implemented to obtain a three dimensional imaged volume of an object in one embodiment.

FIG. 2 is another block diagram of the ultrasound system 100 shown in FIG. 1 implemented to obtain ultrasound data representative of a three dimensional volume 200 of an object 202 in one embodiment. The imaged volume 200 at least partially encompasses the object 202. For example, the object 202 may be disposed entirely within the imaged volume 200 or partially outside of the imaged volume 200. In one embodiment, the object 202 is a moving object, such as a periodically moving object, or an object that repeatedly moves according to time phases. For example, the object 202 may be a beating fetal heart that moves according to repeated phases such as the diastole and systole phases of the fetal heart. Alternatively, the object 202 may be another moving body, such as an adult heart or a non-periodically moving object. The imaged volume 200 may be spatially defined by a two-dimensional dividing plane 204 and two-dimensional end planes 206, 208 disposed on opposite sides of the dividing plane 204. As shown in FIG. 2, the dividing plane 204 is located approximately equidistant from each of the end planes 206, 208.

The beamforming module 110 directs the transmitter 102 to steer ultrasound pulses emitted by one or more of the transducer elements 104 in the ultrasound probe 106 along several two-dimensional image planes 210 that extend through the imaged volume 200. In one embodiment, the ultrasound pulses emitted by the transducer elements 104 are steered along the direction 126 (such as an elevational, azimuthal, or lateral direction) to obtain several spatially diverse sets of ultrasound data, such as image planes 210, between the end planes 206, 208 and/or the dividing plane 204. While the description herein focuses on the sets of ultrasound data being acquired as image planes, alternatively, the sets of ultrasound data may include less than an entire image plane. One or more sets of ultrasound data may include the ultrasound data acquired by transmitting an ultrasound pulse from an individual transducer element or a number of transducer elements that is insufficient to acquire an entire image plane. For example, a set of ultrasound data may include the data acquired from transmission of a single ultrasound beam or a number of ultrasound beams that is insufficient to generate an entire image plane. Therefore, the references to image planes may equally apply to ultrasound data acquired by transmission of one or more ultrasound beams.

As described below, the image planes 210 are combined with each other, such as by interleaving the image planes 210, to form the three-dimensional imaged volume 200. The number of image planes 210 shown in FIG. 2 is provided merely as an example and is not intended to be limiting on all embodiments described herein.

The beamforming module 110 steers the ultrasound pulses in order to receive the ultrasound echoes along the image planes 210. The ultrasound echoes received from pulses directed along an image plane 210 are communicated to the receiver 108 and the beamforming module 110 as acquired ultrasound image data, and then to the processor 112, buffer 114, and the signal processor 116, as described above. The ultrasound echoes are used to form the two-dimensional images represented by the image planes 210. The spatial location of the image planes 210 may be stored or associated with the acquired ultrasound image data for each image plane 210. The spatial location can be used to determine where each image plane 210 is acquired within the imaged volume 200.

In operation, the beamforming module 110 may electrically steer the ultrasound pulses and receive resultant echoes along several image planes 210 over an acquisition time period. The acquisition time period may be sufficiently long that the object 202, such as a periodically moving object, moves through one or more cycles of periodic motion. For example, if the object 202 is a beating fetal heart, the acquisition time period may be sufficiently long (e.g., 0.4 to 6 seconds) such that the heart moves through a plurality of cardiac cycles. Different image planes 210 of the imaged volume 200 are acquired at different spatial locations and/or at different times within the acquisition time period.

Figure 3:
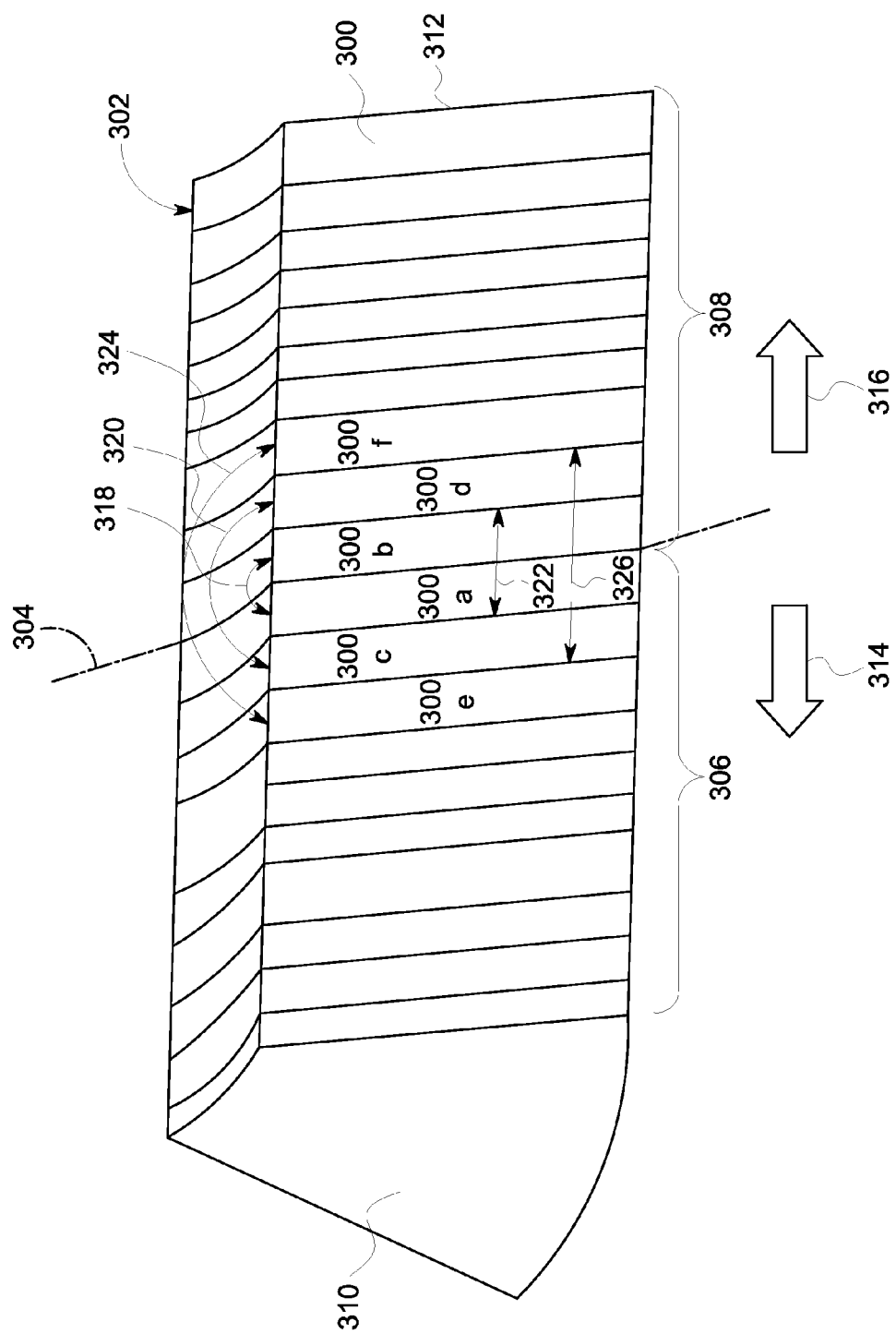
FIG. 3 illustrates a series of image planes of an imaged volume in accordance with one embodiment.

FIG. 3 illustrates a series of image planes 300 of an imaged volume 302 similar to the image planes 210 of the imaged volume 200 of FIG. 2 in accordance with one embodiment. The beamforming module 110 (shown in FIG. 1) steers the ultrasound pulses to acquire the several image planes 300 of an imaged object, such as a fetal heart, over the acquisition time period. As described above, the acquisition time period may extend over several periodic movements of the object, such as by extending over several cardiac cycles of a fetal heart. Different image planes 300 are acquired at different times and, therefore, may be acquired during different temporal phases of the periodically moving object. Additionally, the different image planes 300 are disposed in different locations within the imaged volume 302, as shown in FIG. 3.

In one embodiment, the beamforming module 110 (shown in FIG. 1) steers the ultrasound pulses to acquire the image planes 300 in an alternating, or non-linear, sequence. The alternating sequence can include sequentially obtaining image planes in different, non-overlapping zones of an imaged volume in a near simultaneous manner. For example, the beamforming module 110 may steer ultrasound pulses along two different image planes 300 that are spaced apart and disposed on opposite sides of a dividing plane 304 of the imaged volume 302 in a relatively short time period, such as within 10 milliseconds or less, within 20 milliseconds or less, or within 30 milliseconds or less.

In the illustrated embodiment, the imaged volume 302 may include two non-overlapping volumetric zones 306, 308. Alternatively, the volume 302 may include a greater number of zones 306, 308. The zone 306 extends from the dividing plane 304 to a first end plane 310 of the imaged volume 302 and the zone 308 extends from the dividing plane 304 to an opposite end plane 312 of the imaged volume 302. The beamforming module 110 (shown in FIG. 1) can steer emitted ultrasound pulses to acquire groups of image planes 300, where each group of image planes 300 including sequentially acquired image planes 300 with at least one image plane 300 located in a different zone 306, 308. In another embodiment, each group of image planes 300 may include a plurality of image planes 300 acquired on at least one side of the dividing plane 304. Alternatively, the zones 306, 308 may at least partially overlap such that one or more image planes 300 are shared by a plurality of the zones 306, 308.

The beamforming module 110 (shown in FIG. 1) may steer the ultrasound pulses to acquire a first group 318 of image planes 300a, 300b. As shown in FIG. 3, the image plane 300a is located in the zone 306 while the image plane 300b is located in the zone 308. The image plane 300a may be acquired before the image plane 300b, or vice-versa. The image planes 300a, 300b in the first group 318 can be acquired in a near simultaneous manner, such as by acquiring the image planes 300a, 300b in temporally adjacent, or subsequent, frames when the beamforming module 110 acquires image frames 300 at a frame rate. In one embodiment, if the beamforming module 110 is steering the ultrasound pulses to acquire the image planes 300 at a rate of 120 to 150 Hz or greater, then the image planes 300a, 300b may be acquired within 10 milliseconds or less of each other, within 20 milliseconds or less of each other, or within 30 milliseconds or less of each other, for example.

After acquiring the first group 318 of image planes 300a, 300b, the beamforming module 110 (shown in FIG. 1) acquires a second group 320 of image planes 300c, 300d. As shown in FIG. 3, the image planes 300c, 300d of the second group 320 are located in the different zones 306, 308. The image plane 300c may be acquired before the image plane 300d, or vice-versa. Similar to the first group 318 of image planes 300a, 300b, the image planes 300c, 300d may be sequentially acquired in a near simultaneous manner. The image planes 300c, 300d are spaced apart from each other in the illustrated embodiment. For example, the image planes 300c, 300d may be separated by a separation distance 322. The separation distance 322 can represent an angular distance between the image planes 300c, 300d. Alternatively, the separation distance 322 can represent a linear distance between the image planes 300c, 300d within a plane of the object 202 (shown in FIG. 2) being imaged. In the illustrated embodiment, the image planes 300a, 300b of the first group 318 are adjacent to each other or spaced closer together than the image planes 300c, 300d of the second group 320.

After acquiring the second group 320 of image planes 300c, 300d, the beamforming module 110 (shown in FIG. 1) acquires a third group 324 of image planes 300e, 300f. As shown in FIG. 3, the image planes 300e, 300f of the third group 324 are located in the different zones 306, 308. The image plane 300e may be acquired before the image plane 300f, or vice-versa. Similar to the first and second groups 318, 320, the image planes 300e, 300f may be sequentially acquired in a near simultaneous manner. The image planes 300e, 300f are spaced apart from each other by a separation distance 326. In the illustrated embodiment, the image planes 300e, 300f of the third group 324 are spaced farther apart than the image planes 300c, 300d of the second group 320, which are spaced farther apart than the image planes 300a, 300b of the first group 318.

The beamforming module 110 (shown in FIG. 1) may continue to acquire additional groups of image planes 300, with the image planes 300 in each group acquired from different zones 306, 308 and/or acquired in a near simultaneous manner. The electric steering of the ultrasound pulses can permit the beamforming module 110 to acquire spaced apart image planes 300 in each group in the near simultaneous manner. In the illustrated embodiment, the beamforming module 110 proceeds to acquire the additional groups of image planes 300 in an outward progression. By "outward progression," it is meant that the image planes 300 in subsequently acquired groups are separated by a greater separation distance (such as the separation distances 322, 326) than one or more previously acquired groups of image planes. As shown in FIG. 3, the image planes 300 that are acquired in the zone 306 are sequentially acquired along a direction represented by the arrow 314 while the image planes 300 that are acquired in the zone 308 are sequentially acquired along a direction represented by the arrow 316. The arrows 314, 316 represent directions that extend from the dividing plane 304 toward different end planes 310, 312. In the illustrated outward progression, the separation distance between the image frames 300 in subsequently acquired groups increases. For example, the separation distance in a first acquired group may be smaller than the separation distance of a second acquired group, which can be smaller than the separation distance in a third acquired group, and so on.

The image planes 300 in the groups may be non-intersecting planes. By "non-intersecting," it is meant that the paths that ultrasound pulses are steered along the image planes 300 in each group do not intersect each other outside of the ultrasound probe or transducer elements. For example, the beamforming module 110 may steer ultrasound pulses from the ultrasound probe in diverging paths leading away from each other into the volume 302.

Figure 4:
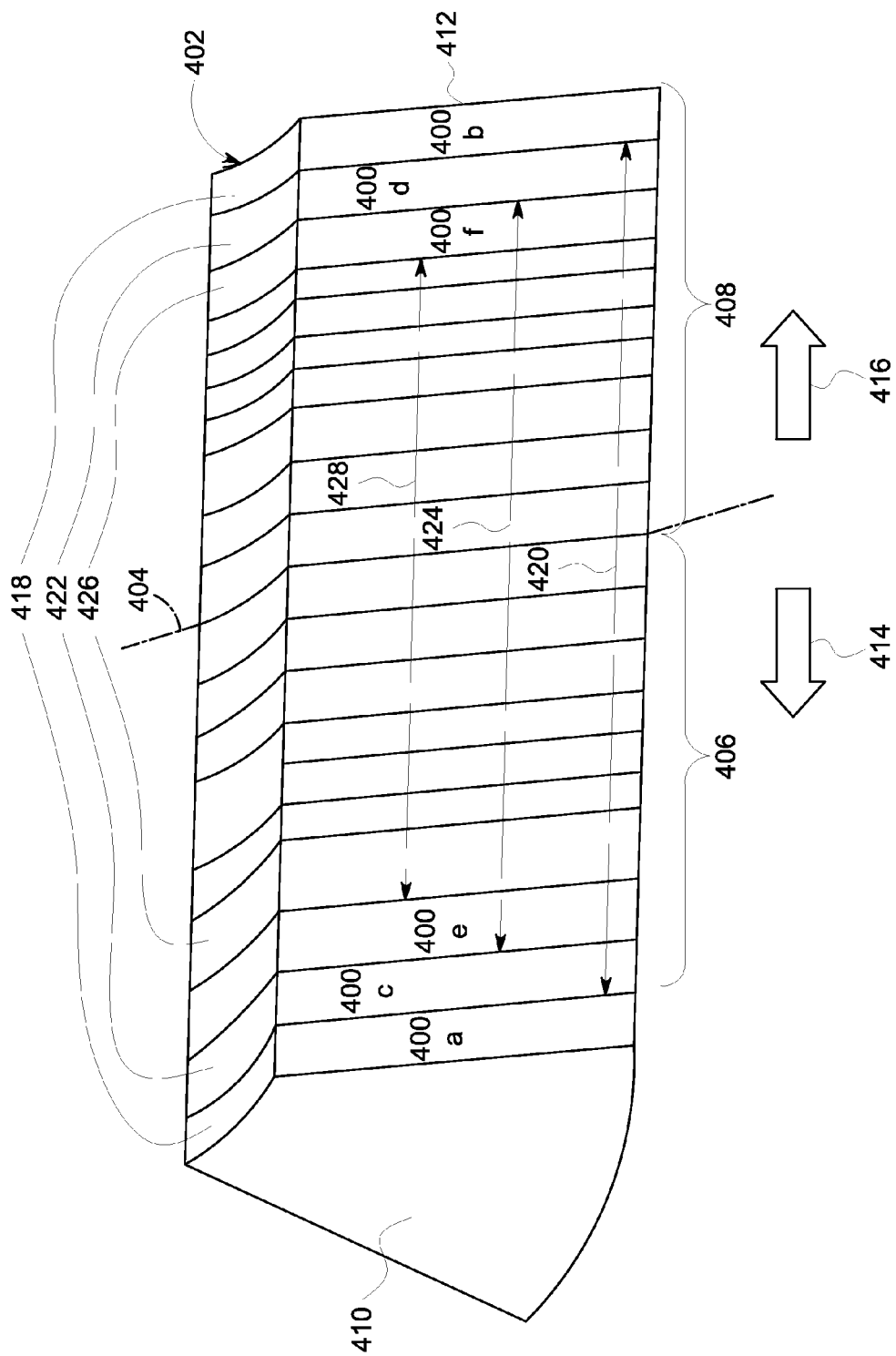
FIG. 4 illustrates a series of image planes of an imaged volume in accordance with another embodiment.

FIG. 4 illustrates a series of image planes 400 acquired in accordance with another embodiment. FIG. 4 illustrates another sequence in which the beamforming module 110 (shown in FIG. 1) may steer the ultrasound pulses to acquire the image planes 400 in the imaged volume 402. Similar to the imaged volume 302 (shown in FIG. 3), the imaged volume 402 has a dividing plane 404, opposite end planes 410, 412, and volumetric zones 406, 408.

The beamforming module 110 (shown in FIG. 1) may steer the ultrasound pulses to acquire a first group 418 of non-intersecting image planes 400a, 400b. As shown in FIG. 4, the image plane 400a is located in the zone 406 while the image plane 400b is located in the zone 408. The image plane 400a may be acquired before the image plane 400b, or vice-versa. The image planes 400a, 400b in the first group 418 can be acquired in a near simultaneous manner. The image planes 400a, 400b are separated by a separation distance 420. After acquiring the first group 418 of image planes 400a, 400b, the beamforming module 110 acquires a second group 422 of image planes 400c, 400d. As shown in FIG. 4, the image planes 400c, 400d of the second group 422 are located in the different zones 406, 408. Similar to the first group 418, the image planes 400c, 400d may be sequentially acquired in a near simultaneous manner. The image planes 400c, 400d are spaced apart from each other by a separation distance 424 that is smaller than the separation distance 420 of the first group 418.

After acquiring the second group 422 of image planes 400c, 400d, the beamforming module 110 (shown in FIG. 1) acquires a third group 426 of image planes 400e, 400f. The image planes 400e, 400f of the third group 426 can be located in the different zones 406, 408. The image planes 400e, 400f are spaced apart from each other by a separation distance 428 that is smaller than the separation distance 424 of the second group 422, which is smaller than the separation distance 420 of the first group 418.

The beamforming module 110 (shown in FIG. 1) may continue to acquire additional groups of image planes 400, with the image planes 400 in each group acquired from different zones 406, 408 and/or acquired in a near simultaneous manner. The electric steering of the ultrasound pulses can permit the beamforming module 110 to acquire spaced apart image planes 400 in each group in the near simultaneous manner. In the illustrated embodiment, the beamforming module 110 proceeds to acquire the additional groups of image planes 400 in an inward progression. By "inward progression," it is meant that the image planes 400 in subsequently acquired groups are separated by a smaller separation distance (such as the separation distances 420, 424, 428) than one or more previously acquired groups of image planes. As shown in FIG. 4, the image planes 400 that are acquired in the zone 406 are sequentially acquired along a direction represented by the arrow 414 while the image planes 400 that are acquired in the zone 408 are sequentially acquired along a direction represented by the arrow 416. The arrows 414, 416 represent directions that extend from the respective end planes 410, 412 toward the dividing plane 404.

In the illustrated inward progression, the separation distance between the image frames 400 in subsequently acquired groups decreases. For example, the separation distance in a first acquired group may be larger than the separation distance of a second acquired group, which can be larger than the separation distance in a third acquired group, and so on.

While the inward and outward progressions of acquiring groups of image planes in FIGS. 3 and 4 provide some examples of the order in which the image planes may be acquired, the illustrated examples are not intended to encompass all embodiments of the disclosed subject matter. Other progressions may be used. For example, one or more progressions may acquire image planes in different volumetric zones in the same direction as opposed to the opposite directions described in connection with FIGS. 3 and 4. In another example, the progressions may begin in one volumetric zone and terminate in another volumetric zone. For example, the progression may begin with an image plane in the center of a first volumetric zone and continue by acquiring image planes in a direction that extends to the dividing plane of the imaged volume and proceeds to linearly continue through a second volumetric zone.

Returning to the discussion of the ultrasound system 100 shown in FIG. 2, the beamforming module 110 may acquire the image planes 210 within each group of image planes within a relatively short time period of each other. A frame rate of the ultrasound system 100 represents the speed at which the ultrasound system 100 acquires image planes 210. For example, if the ultrasound system 100 has a frame rate of 120 Hz, then the ultrasound system 100 may acquire image planes 210 at a rate of approximately 120 image planes per second. Alternatively, the ultrasound system 100 may have a different frame rate, such as between 60 Hz to 150 Hz, although slower or faster rates may be used.

Acquiring the image planes 210 within each group at approximately the same time may cause the image planes 210 to be acquired within the same temporal phase of a periodically moving object 202. For example, acquiring image planes 210 in the same group within 10 to 30 milliseconds of each other may result in the image planes 210 in the group being acquired during a common phase, such as within the same diastole or systole phase of a fetal heart. As the beamformer 110 steers the ultrasound pulses through the imaged volume 200 (such as by following an alternating sequence described above), multiple groups of image planes 210 may be acquired in different locations within the imaged volume 200 and at different times relative to each other. As a result, different groups of image planes 210 may represent images of the object 202 in different locations and/or during different temporal phases of periodic motion of the object 202. The beamformer 110 may direct the transducer elements 104 to acquire the image planes 210 over a sufficiently long time period that the object 202 moves through several phases of a periodic motion. For example, for a fetal heart beating at a rate of 125 to 175 beats per minute, the image planes 210 may be acquired over a 3 to 6 second acquisition time period in order to acquire image planes 210 during 6 to 12 cardiac cycles of the fetal heart. Alternatively, a longer or shorter acquisition time period may be used. Acquisition of the image planes 210 over such an acquisition time period can result in several groups of image planes 210 being obtained in different locations of the object 202, but with the image planes 210 representative of the same temporal phase of the object 202.

In one embodiment, the ultrasound system 100 obtains the groups of image planes 210 at a sufficiently fast rate such that the acquisition time period required to obtain several three-dimensional volumes 200 of the object 202 may be reduced. For example, frame rates of approximately 120 Hz to 150 Hz or greater and/or the electric steering of the ultrasound pulses may permit the ultrasound system 100 to acquire multiple groups of spaced apart, or non-adjacent image planes 210 in different, non-overlapping zones of the volume being imaged within the same time period or temporal phase of a periodically moving object 202. In one embodiment, the ultrasound system 100 acquires multiple groups of the image planes 210 in different locations of the volume 200 within the same diastole or systole phase of a fetal heart. Increasing the number of spatially diverse image planes 210 of the volume 200 within a relatively short time period can reduce the acquisition time period required to obtain imaged volumes 200 that include different temporal phases of the periodically moving object 202.

The signal processor 116 includes a timing module 212 and a spatial and temporal image correlation module 214 ("STIC module"). The timing module 212 and/or the STIC module 214 may be embodied in one or more sets of instructions stored on a tangible and/or non-transitory computer readable storage medium, such as a computer hard drive, RAM, ROM, EEPROM, flash drive, or other memory device, that direct the signal processor 116 (e.g., a computer processor or controller) to perform one or more operations. Alternatively, the timing module 212 and/or STIC module 214 may be embodied as instructions that are hard wired in the signal processor 116.

The timing module 212 identifies temporal relationships between the image planes 210 and/or between the groups of the image planes 210. The temporal relationships represent the different times at which the image planes 210 are acquired. As described above, some image planes 210 may be acquired at approximately the same time (e.g., image planes 210 of a common group that are acquired within 20 or 10 milliseconds or less of each other). Other image planes 210 may be acquired at different times (e.g., image planes 210 in other groups or image planes 210 that are acquired with a time difference between acquisition of the image planes 210 that is more than 10 or 30 milliseconds). The timing module 212 determines when each image plane 210 is obtained relative to one or more other image planes 210. For example, the timing module 212 can track the times at which the different image planes 210 are obtained as the image planes 210 are acquired. The timing module 212 may associate each image plane 210 with a temporal characteristic representative of the time at which the image plane 210 is acquired. For example, the timing module 212 may associate the image planes 210 with times at which the image planes 210 were obtained.

The STIC module 214 receives the groups of image planes 210 and the temporal characteristics of the image planes 210 from the timing module 212. Based on the temporal and spatial characteristics of the image planes 210, the STIC module 214 combines the two-dimensional image planes 210 into one or more three-dimensional imaged volumes 200. The STIC module 214 may combine or interleave the image planes 210 acquired at the same time or approximately the same time, or at the same phase or approximately the same phase of a periodically moving body, to form an imaged volume 200. For example, if the object 202 being imaged is a periodically moving body, the STIC module 214 may combine or interleave the image planes 210 obtained during a common phase of the periodic movement of the object 202 into a first imaged volume 200, the image planes 210 obtained during another common phase into a second imaged volume 200, and so on.

Figure 5:
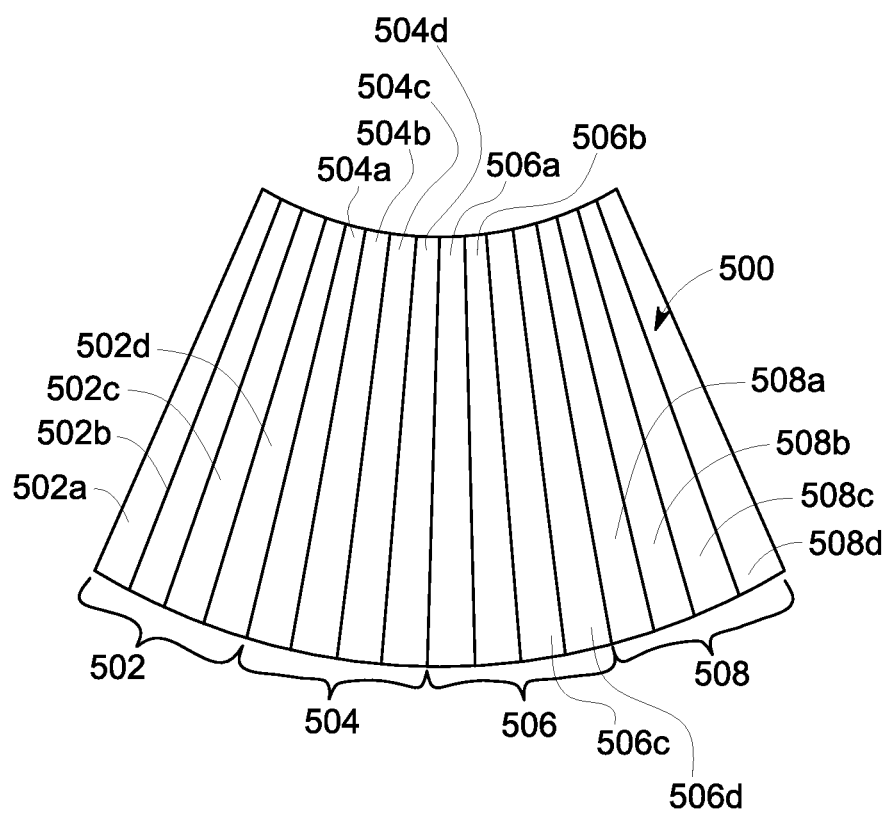
FIG. 5 illustrates a temporal series of several image planes.

FIG. 5 illustrates a temporal series of several image planes 500 that are similar to the image planes 210 of FIG. 2. The image planes 500 may be acquired in groups at different times and/or during different temporal phases of a periodically moving body, as described above. The STIC module 214 may organize the image planes 500 into temporal groups 502, 504, 506, 508 based on the temporal relationships of the image planes 500. In the embodiment shown in FIG. 5, the image planes 500 are arranged based on the times at which the image planes 500 are acquired and not necessarily by the locations where the image planes 500 are acquired. For example, a first temporal group 502 includes image planes 502a, 502b, 502c, 502d that were acquired in different locations of an imaged volume but during a common temporal phase of the imaged body 202 (shown in FIG. 2). A second temporal group 504 includes the image planes 504a, 504b, 504c, 504d acquired in different locations but during a common temporal phase that differs from the first temporal group 502. A third temporal group 506 includes image planes 506a, 506b, 506c, 506d acquired in different locations but during a common temporal phase that differs from the first and second temporal groups 502, 504. A fourth temporal group 508 includes the image planes 508a, 508b, 508c, 508d acquired in different locations but during a common temporal phase that differs from the first, second, and third temporal groups 502, 504, 506. When imaging a fetal heart or other anatomy as discussed previously, however, many more image planes may be acquired within each temporal group 502, 504, 506, 508.

Once the STIC module 214 has temporally organized the image planes 500, or grouped the image planes 500 based on acquisition time, the STIC module 214 may spatially arrange the image planes 500 based on where the image planes 500 were acquired. The STIC module 214 may combine or interleave the image planes 500 within each temporal group 502, 504, 506, 508 to form a different three-dimensional imaged volume. For example, the STIC module 214 can combine the image planes 500 acquired at the same phase, or point in time within a cardiac cycle, but from a different lateral position, into a volume. In the illustrated embodiment, the image planes 502a, 502b, 502c, 502d of the first temporal group 502 may have been acquired during the same phase within a cardiac cycle but in different locations while the image planes of the other temporal groups 504, 506, 508 may have been acquired in the same or similar locations as the image planes in the temporal group 502 but during different phases of the cardiac cycle.

In another embodiment, the STIC module 214 may organize the acquired ultrasound image data obtained by individual transducer elements 104 into different temporal groups based on when the ultrasound image data obtained by each transducer element 104 was obtained. For example, similar to the temporal organization of the image planes, the STIC module 214 may arrange the ultrasound image data based on when each transducer element 104 acquired the ultrasound image data. The temporally organized ultrasound image data may then be combined to form three-dimensional imaged volumes based on where each ultrasound image data was obtained.

Figure 6:
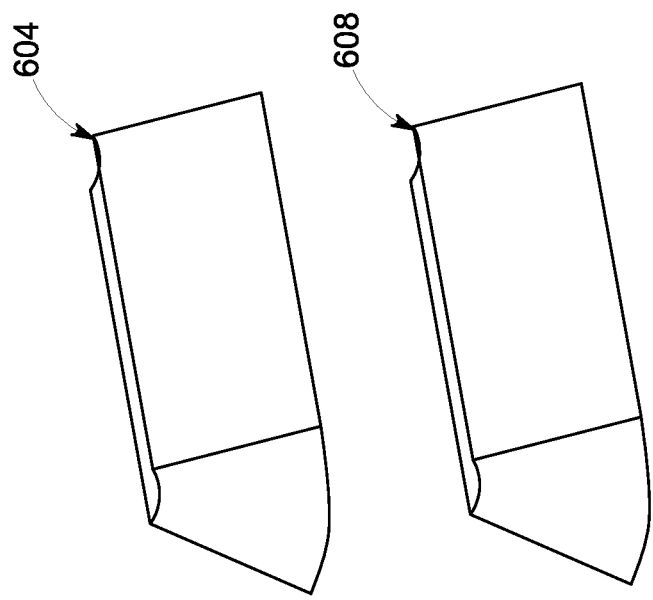
FIG. 6 illustrates several volumes that correspond to temporal groups shown in FIG. 5.
Figure 6:
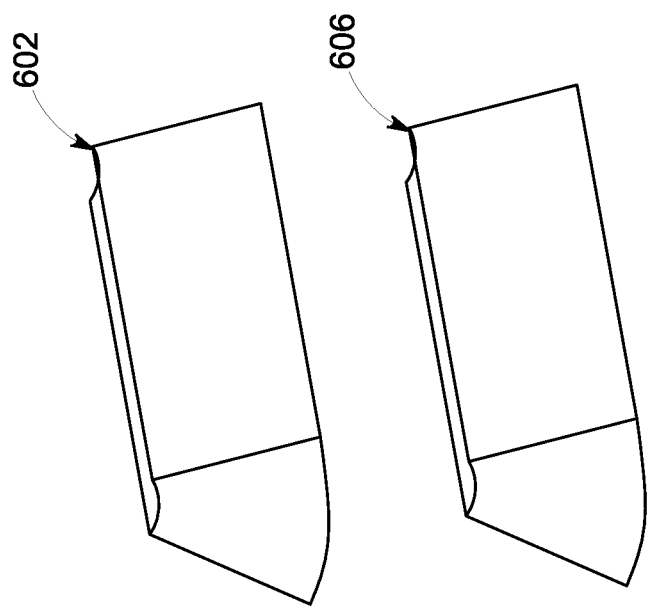

FIG. 6 illustrates several volumes 602, 604, 606, 608 that correspond to the temporal groups 502, 504, 506, 508 of the image planes 500. The volumes 602, 604, 606, 608 represent different three-dimensional imaged volumes (such as the imaged volume 200 shown in FIG. 2) obtained at different temporal phases. For example, each of the volumes 602, 604, 606, 608 may be formed from the two-dimensional image planes 500 in a different temporal group 502, 504, 506, 508 (shown in FIG. 5). As a result, each volume 602, 604, 606, 608 may include acquired ultrasound image data from a different time of the periodic motion of an imaged body, such as a different time during a cardiac cycle of a fetal heart.

In order to form the volumes 602, 604, 606, 608, the STIC module 214 (shown in FIG. 2) combines the image planes 500 (shown in FIG. 5) of each temporal group 502, 504, 506, 508 (shown in FIG. 5) into a different volume. For example, with respect to FIG. 5, the image planes 502a-502d of the first temporal group 502 are combined into the volume 602, the image planes 504a-504d of the second temporal group 504 are combined into the volume 604, the image planes 506a-506d of the third temporal group 506 are combined into the volume 606, and the image planes 508a-508d of the fourth temporal group 508 are combined into the volume 608. Each volume 602, 604, 606, 608 can provide a three-dimensional image or snapshot of the fetal heart at a particular phase during one single beat of the cardiac cycle, in one embodiment. While only four volumes 602, 604, 606, 608 are shown, alternatively a smaller or larger number of volumes 602, 604, 606, 608 may be acquired.

The volumes 602, 604, 606, 608 may be displayed by the display system 118 (shown in FIG. 1) in three orthogonal planes in a cycle, such as a cineloop, which allows an operator to navigate through the volumes 602, 604, 606, 608 and/or view individual volumes 602, 604, 606, 608. Alternatively, the image planes may be processed and displayed in other ways. For example, the display system 118 may render the image data to show the inner 3D structure of the heart. For example, maximum intensity projection, minimum intensity projection, average projection, and the like may be calculated and displayed. A single volume 602, 604, 606, 608, or a portion or slice of a volume 602, 604, 606, 608, may be selected for display. The selected portion may be rotated on the display system 118 or further processed separate from the remaining volume data. In addition, an anatomic M-mode image representing a single selected line within the volumes 602, 604, 606, 608 may be displayed over time.

The volumes 602, 604, 606, 608 may be combined in a temporal series and stored in a memory, such the buffer 122, or on a server on a network. The series of volumes 602, 604, 606, 608 and/or the unprocessed volumetric data may also be transferred via a network or a portable disc to be further processed and reviewed at a different location after the patient has left the examination. Having the data available to be reviewed and processed later can be advantageous, especially during early pregnancy, when the relationship between fetus and amniotic fluid allows a lot of movement.

The acquisition time required to obtain a predetermined number of volumes 602, 604, 606, 608 during an ultrasound examination can vary based on the number of image planes that are acquired for each volume 602, 604, 606, 608 and/or the image resolution desired for the volumes 602, 604, 606, 608. In general, a larger number of image planes per volume 602, 604, 606, 608 and/or larger image resolutions for the volumes 602, 604, 606, 608 require longer acquisition times relative to smaller numbers of image planes and/or smaller image resolutions.

Figure 7:
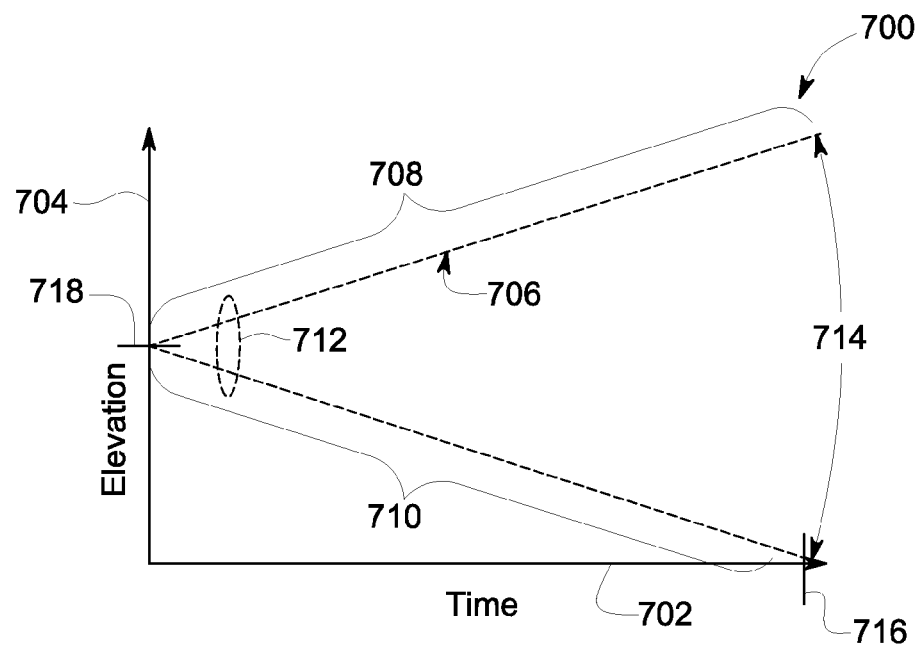
FIG. 7 illustrates one example of an image acquisition schema for acquiring image planes acquired during an ultrasound examination.
Figure 8:
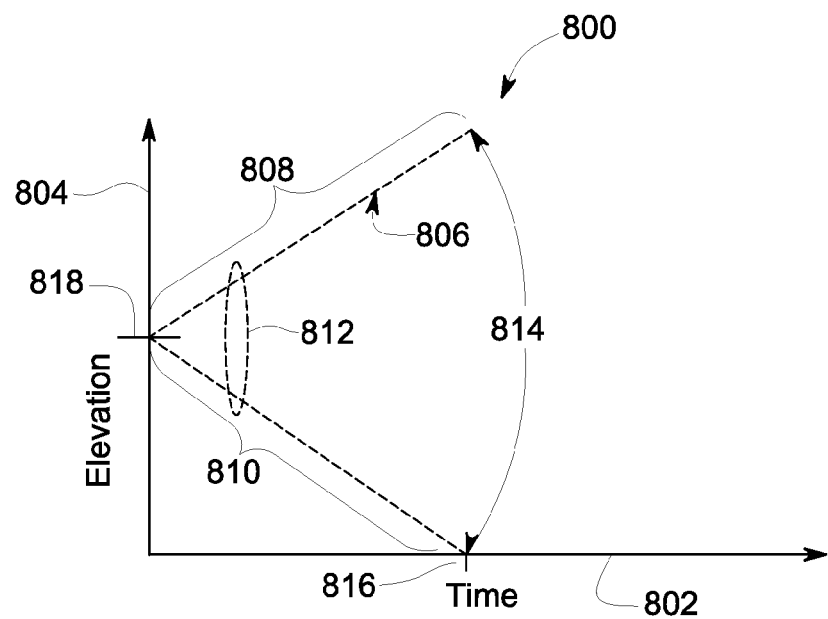
FIG. 8 illustrates another example of an image acquisition schema for acquiring image planes acquired during an ultrasound examination.

FIGS. 7 and 8 illustrate examples of image acquisition schemas 700, 800 for acquiring image planes acquired during an ultrasound examination. The acquisition schemas 700, 800 are used to acquire multiple groups of image planes at various temporal phases of a periodically moving object in order to create a plurality of three-dimensional imaged volumes of the object at a plurality of the temporal phases.

The acquisition schemas 700, 800 are shown near horizontal axes 702, 802 representative of time and vertical axes 704, 804 representative of an elevational direction. The acquisition schemas 700, 800 are shown in dotted lines comprised of markers 706, 806 to represent when each elevational image plane is acquired during an ultrasound examination. For example, each marker 706, 806 of the acquisition schemas 700, 800 may represent acquisition of an image plane at a different location, such as a different elevational location within an imaged volume.

The acquisition schemas 700, 800 each include diverging legs 708, 710 and diverging legs 808, 810, respectively. Each leg 708, 710, 808, 810 represents the elevational image planes obtained from a different, non-overlapping zone of an imaged volume. For example, with reference to the imaged volume 302 shown in FIG. 3, the markers 706 within the diverging leg 708 of the acquisition schemas 700 may represent the different image planes 300a, 300c, and so on, obtained within the zone 306 while the markers 706 within the diverging leg 710 may represent the different image planes 300b, 300d, and so on, obtained within the zone 308. Similarly, the markers 806 within the diverging leg 808 of the schema 800 may represent the different image planes 300a, 300c, and so on, obtained within the zone 306 while the markers 806 within the diverging leg 810 may represent the different image planes 300b, 300d, and so on, obtained within the zone 308.

A vertical group 712, 812 shown in FIGS. 7 and 8 represents the groups of image planes that are acquired simultaneously or at approximately the same time, such as within 10 to 30 milliseconds or less of each other. For example, with respect to FIG. 3, the vertical group 712 or 812 may represent the image planes 300a, 300b of a common group and that are sequentially obtained at approximately the same time. As shown in FIGS. 7 and 8, several vertical groups 712, 812 include markers 706, 806 in each of the diverging legs 708, 710 and 808, 810.

The diverging legs 708, 710 and 808, 810 extend from the vertical axes 704, 804 to end points 714, 814. The end points 714, 814 represent the last image planes acquired during an ultrasound examination. An acquisition time 716, 816 represents the time periods over which the diverging legs 708, 710 and 808, 810, respectively, extend from the vertical axes 704, 804 to the end points 714, 814. As shown by comparing the schemas 700, 800, the schema 700 has a longer acquisition time 716 than the acquisition time 816 of the schema 800. However, the schema 700 also provides more image planes than the schema 800. For example, if the schemas 700, 800 acquire image planes at the same frame rate, the schema 700 acquires more image planes than the schema 800 as the schema 700 has a longer acquisition time 716. Acquiring more image planes may provide the imaged volumes that are created using the schema 700 with greater resolution than the imaged volumes created using the schema 800. On the other hand, the schema 800 may provide sufficient resolution in the imaged volumes created using the schema 800 while having a significantly shorter acquisition time 816.

In the illustrated embodiment, the diverging legs 708, 710 intersect at a dividing plane 718 and the diverging legs 808, 810 intersect at a dividing plane 818. The dividing planes 718, 818 may represent the dividing plane 304 (shown in FIG. 3) of the volume 302 (shown in FIG. 3). Alternatively, the diverging legs 708, 710 and/or the diverging legs 808, 810 may intersect at a location that corresponds to a positive or negative acquisition time along the horizontal axes 702, 802.

Figure 9:
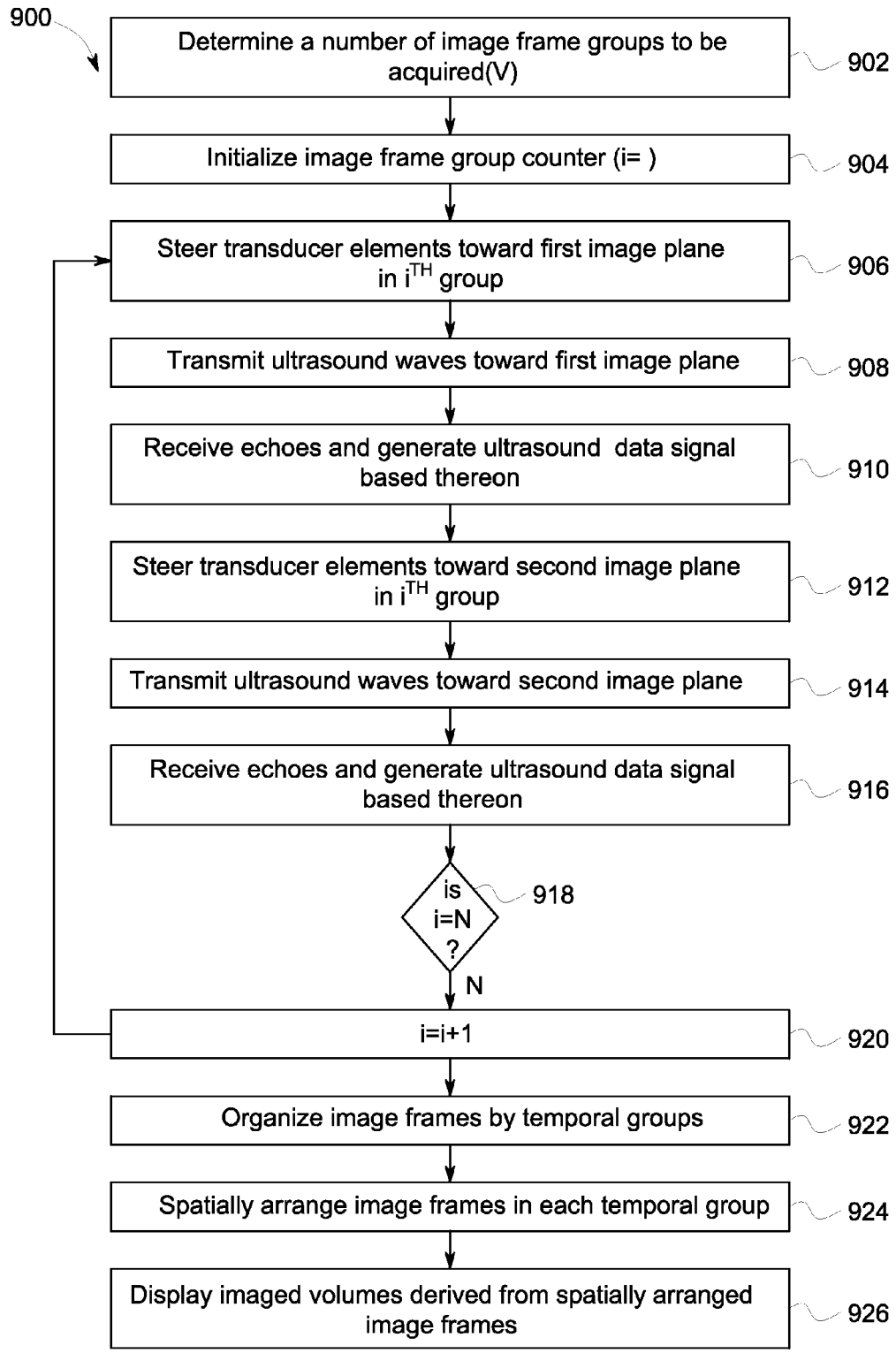
FIG. 9 is a flowchart of one embodiment of a method for ultrasound imaging.

FIG. 9 is a flowchart of one embodiment of a method 900 for ultrasound imaging. The method 900 may be used in conjunction with the ultrasound system 100 (shown in FIG. 1) to acquire plural three-dimensional imaged volumes of different temporal phases of a periodically moving object, such as a fetal heart, in a relatively short acquisition time period, as described above.

At 902, a number of image plane groups (N) to be acquired in the imaged volumes of the object is determined. For example, the total number of groups of image planes 210 (shown in FIG. 2) that is to be obtained from the imaged volume 200 (shown in FIG. 2) may be input by an operator. Alternatively, the total number of groups of image planes may be a predetermined or default number associated with the ultrasound system 100 (shown in FIG. 1). In another embodiment, the total number of groups of image planes may be automatically determined based on the type of object 202 (shown in FIG. 2) being imaged. In the illustrated embodiment, the letter "N" represents the total number of groups of image planes that is acquired for the imaged volumes.

At 904, an image plane group counter (i) is initialized. The image plane group counter may be used to determine which groups of image planes have been acquired or are scheduled to be acquired. In the illustrated embodiment, the letter "i" represents the image plane group counter. The image plane group counter may be initialized by setting the value of the image plane group counter to 1. Alternatively, a different number may be used.

At 906, one or more ultrasound pulses are steered toward a first image plane in the $i^{TH}$ group of image planes. For example, the beamforming module 110 (shown in FIG. 1) may electrically steer one or more ultrasound pulses toward a first image plane 210 (shown in FIG. 2) (e.g., a first elevational, azimuthal, or lateral direction) in the imaged volume 200 (shown in FIG. 2). The first image plane 210 may be located at or near a dividing plane of the imaged volume, at or near end planes of the imaged volume, or at another location between the dividing plane and the end planes.

At 908, ultrasound waves are transmitted toward the first image plane of the $i^{TH}$ group. For example, one or more ultrasound pulses that are steered toward the first image plane of the $i^{TH}$ group may be directed toward the first image plane.

At 910, echoes of the ultrasound waves are received by one or more of the transducer elements and ultrasound image data is created based on the echoes. For example, one or more transducer elements 104 (shown in FIG. 1) may receive echoes of the ultrasound waves that are transmitted toward the first image plane 210 (shown in FIG. 1) of the $i^{TH}$ group and are reflected off of the object 202 (shown in FIG. 2) being imaged. The transducer elements 104 and the ultrasound probe 106 (shown in FIG. 1) can convert the echoes into analog and/or digital signals representative of the varying intensities of the received echoes. These signals may include data referred to as acquired ultrasound image data.

At 912, one or more ultrasound pulses are steered toward a second image plane in the $i^{TH}$ group of image planes. For example, the beamforming module 110 (shown in FIG. 1) may electrically steer one or more ultrasound pulses toward a second image plane 210 (shown in FIG. 2) (e.g., a first elevational, azimuthal, or lateral direction) in the imaged volume 200 (shown in FIG. 2). The second image plane 210 may be located at or near a dividing plane of the imaged volume, at or near end planes of the imaged volume, or at another location between the dividing plane and the end planes. As described above, the first and second image planes 210 in the $i^{TH}$ group may be located in different zones of the imaged volume. For example, the first image plane 210 may be disposed in a first zone of the imaged volume while the second image plane 210 is disposed in a second, non-overlapping zone of the imaged volume. The method 900 may alternate back and forth to sequentially acquire image frames in each group in different zones of the imaged volume.

At 914, ultrasound waves are transmitted toward the second image plane of the $i^{TH}$ group. For example, one or more ultrasound pulses may be steered toward the second image plane of the $i^{TH}$ group.

At 916, echoes of the ultrasound waves are received by one or more of the transducer elements and ultrasound image data is created based on the echoes. For example, one or more transducer elements 104 (shown in FIG. 1) may receive echoes of the ultrasound waves transmitted toward the second image plane 210 (shown in FIG. 2) of the $i^{TH}$ group that are reflected off of the object 202 (shown in FIG. 2) being imaged. The transducer elements 104 and the ultrasound probe 106 (shown in FIG. 1) can convert the echoes into analog and/or digital signals representative of the varying intensities of the received echoes.

If the $i^{TH}$ image group includes more than two image planes, then the method 900 may continue to steer more ultrasound pulses toward third, fourth, fifth, and so on, image planes of the $i^{TH}$ group to acquire ultrasound image data from each of the image planes in the $i^{TH}$ image group.

At 918, the image plane group counter (i) is compared to the number of image planes to be acquired from the imaged volume (N). For example, the counter may be compared to the number of image planes to determine if all of the image planes have been acquired. If the image plane group counter (i) is less than the number of image planes to be acquired from the imaged volume (N), then the image plane group counter (i) may indicate that not all image planes that were to be acquired have been so acquired. As a result, flow of the method 900 continues to 920.

At 920, the value of the image plane group counter is incrementally increased. For example, the value of i may be increased by one according to the following equation:

$$i = i+1 \qquad \text{(Eqn. 1)}$$

Flow of the method 900 may return to 906, where one or more ultrasound pulses are steered to obtain the first image plane of the $i^{TH}$ image frame group. Increasing the value of the image frame group at 920 causes the method 900 to obtain the image frames of the next image frame group when the method 900 returns to 906. The method 900 may continue in a loop-wise manner to acquire image frames from N total image frame groups by incrementally increasing the value of the image plane group counter (i) and acquiring the image planes for each image plane group.

Alternatively, if the value of the image plane group counter (i) is equivalent to the number of image planes to be acquired (N), then the value of the image plane group counter (i) may indicate that all image planes that were to be acquired in the imaged volume have been obtained. As a result, flow of the method 900 may continue to 922.

At 922, the acquired image frames from the N image frame groups are organized into temporal groups. For example, as described above, the image frames may be arranged into temporal groups based on when the image frames were acquired. The image frames that were acquired in or during the same temporal phase of a periodically moving object may be grouped into the same temporal group. Alternatively, the image frames that were acquired within a predetermined time window of each other may be collected into the same temporal group.

At 924, the image frames within each temporal group are spatially arranged to form three-dimensional imaged volume for each temporal group. For example, the image frames that were acquired at the same temporal phase or within a predetermined time period of each other may be interleaved or combined with each other to reconstruct a three-dimensional image of the object during the temporal phase or time period at which the image frames were obtained. If several temporal groups are obtained, then several three-dimensional volumes may be constructed.

At 926, the imaged volumes are visually presented to an operator on a display device, such as a monitor. The imaged volumes may be used to visualize snapshots or images of a periodically moving body during different phases of the periodic movement of the body.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter disclosed herein without departing from its scope. While the dimensions and types of materials described herein are intended to define the parameters of the one or more embodiments of the subject matter, they are by no means limiting and are exemplary embodiments. Many other embodiments will be apparent to one of ordinary skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the described subject matter, including the best mode, and also to enable one of ordinary skill in the art to practice the embodiments disclosed herein, including making and using any devices or systems and performing the methods. The patentable scope of the subject matter is defined by the claims, and may include other examples that occur to one of ordinary skill in the art. Such other examples are within the scope of the claims if they have structural elements that do not differ from the literal language of the claims, or if they include equivalent structural elements with insubstantial differences from the literal language of the claims.

What is claimed is:

1. An ultrasound imaging system comprising:
an ultrasound probe including transducer elements configured to emit ultrasound pulses into an imaged volume that includes a heart that periodically moves during cardiac cycles body and receive ultrasound echoes reflected off of the heart, the ultrasound probe configured to acquire different first and second sets of two dimensional ultrasound frame data of the heart during periodic movement of the heart during the cardiac cycles,
wherein each of the first and second sets of the two dimensional ultrasound frame data is acquired by sequentially switching back and forth between obtaining two dimensional ultrasound frame data from a first spatial zone of the heart and obtaining two dimensional ultrasound frame data from a different, non-overlapping second spatial zone of the heart, wherein all of the two dimensional ultrasound frame data in the first set are acquired from the first spatial zone of the heart and all of the two dimensional ultrasound frame data in the second set are acquired from the different, non-overlapping second spatial zone of the heart, wherein the two dimensional ultrasound frame data acquired from the first spatial zone and the two dimensional ultrasound frame data acquired from the second spatial zone for each of the first and second sets are acquired during a single cardiac cycle of the heart;

at least one spatial and temporal image correlation (STIC) processor electrically coupled with the ultrasound probe, the at least one STIC processor configured to:

receive the first and second sets of the two dimensional ultrasound frame data from the ultrasound probe;

organize the two dimensional ultrasound frame data acquired from the first spatial zone;

organize the two dimensional ultrasound frame data acquired from the second spatial zone into a second temporal group;

spatially arrange the two dimensional ultrasound frame data in each of the first and second temporal groups based on where the two dimensional ultrasound frame data were acquired;

combine the two dimensional ultrasound frame data in the first temporal group into a first three-dimensional imaged volume; and combine the two dimensional ultrasound frame data in the second temporal group into a second three-dimensional imaged volume.

2. The system of claim 1, wherein each of the first and second temporal groups includes the two dimensional ultrasound frame data from each of the first and second zones of the imaged volume.

3. The system of claim 1, wherein the at least one STIC processor is configured to electrically steer the ultrasound pulses in a first direction to acquire the first set of the two dimensional ultrasound frame data in a first zone of the imaged volume and to electrically steer one or more of the ultrasound pulses in a different, second direction to acquire the second set of the two dimensional ultrasound frame data in a second zone of the imaged volume.

4. The system of claim 1, wherein the imaged volume includes plural zones separated by a dividing plane and the at least one STIC processor is further configured to sequentially acquire the first and second sets of the two dimensional ultrasound frame data on opposite sides of the dividing plane.

5. A method of ultrasound imaging, the method comprising:

first and second sets of two dimensional ultrasound frame data in an imaged volume that at least partially encompasses a heart that periodically moves during cardiac cycles, the first and second sets of the two dimensional ultrasound frame data obtained by transmitting one or more ultrasound pulses from one or more transducer elements into different, non-overlapping first and second spatial zones of the heart, wherein each of the first and second sets of the two dimensional ultrasound frame data is acquired by sequentially switching back and forth between obtaining the two dimensional frame data from the first spatial zone of the heart and obtaining the two dimensional frame data from the second spatial zone of the heart, wherein all of the two dimensional ultrasound frame data in the first set are acquired from the first spatial zone of the heart and all of the two dimensional ultrasound frame data in the second set are acquired from the second spatial zone of the heart, wherein the two dimensional ultrasound frame data acquired from the first spatial zone and the two dimensional ultrasound frame data acquired from the second spatial zone for each of the first and second sets are acquired during a single cardiac cycle of the heart;

organizing the frame data acquired from the first spatial zone into a first temporal group;

organizing the frame data acquired from the second spatial zone into a second temporal group;

spatially arranging the frame data in each of the first and second temporal groups based on where the frame data were acquired;

combining the frame data in the first temporal group into a first three-dimensional imaged volume; and combining the frame data in the second temporal group into a second three-dimensional imaged volume.

6. The method of claim 5, wherein each of the two dimensional ultrasound frame data represents a single image plane in the imaged volume.

7. The method of claim 5, wherein acquiring the first and second sets of the two dimensional ultrasound frame data includes acquiring the two dimensional ultrasound frame data of the heart and spatially arranging the frame data includes arranging the frame data into the first and second temporal groups associated with different phases of periodic motion of the heart.

8. The method of claim 5, wherein acquiring the first and second sets of the two dimensional ultrasound frame data includes acquiring each of the two dimensional ultrasound frame data in each of the first and second sets from a different zone of the first and second spatial zones such that each of the first and second sets includes a separate two dimensional ultrasound frame data from each of the zones.

9. The method of claim 5, wherein acquiring the first and second sets of the two dimensional ultrasound frame data includes acquiring the two dimensional frame data in each of the sets within 30 milliseconds or less of each other.

10. The method of claim 5, wherein acquiring the first and second sets of the two dimensional ultrasound frame data includes electrically steering one or more of the ultrasound pulses in a first direction to acquire the two dimensional frame data in the first spatial zone of the imaged volume and electrically steering one or more of the ultrasound pulses in a different, second direction to acquire the two dimensional frame data in the second spatial zone of the imaged volume.

11. The method of claim 5, comprising interleaving the two dimensional ultrasound frame data sets in each of the first and second temporal groups to form a different three-dimensional image representative of a different periodic phase of the heart.

12. The method of claim 5, wherein the first and second spatial zones are separated by a dividing plane and acquiring the first and second sets of the two dimensional ultrasound frame data includes sequentially acquiring the two dimensional frame data in each of the first and second sets on opposite sides of the dividing plane.

13. The method of claim 12, wherein the imaged volume extends between opposite end planes with the dividing plane disposed therebetween, and acquiring the first and second sets of the two dimensional ultrasound frame data includes obtaining the two dimensional ultrasound frame data in each of the zones by proceeding in an outward progression from proximate to the dividing plane toward the end planes.

14. The method of claim 12, wherein the imaged volume extends between opposite end planes with the dividing plane disposed therebetween, and acquiring the first and second sets of the two dimensional ultrasound frame data includes obtaining the two dimensional ultrasound frame data in each of the zones by proceeding in an inward progression from proximate to the end planes toward the dividing plane.

15. A computer readable storage medium for an ultrasound imaging system having a spatial and temporal image correlation (STIC) processor, the medium having one or more sets of instructions stored thereon for directing the STIC processor to:
  acquire first and second sets of two dimensional ultrasound data in an imaged volume that at least partially encompasses a heart that periodically moves during cardiac cycles,
  wherein each of the first and second sets of the two dimensional ultrasound data is acquired by sequentially switching back and forth between obtaining two dimensional frame data from a first spatial zone of the heart and obtaining two dimensional frame data from a different, non-overlapping second spatial zone of the heart,
  wherein all of the two dimensional ultrasound frame data in the first set are acquired from the first spatial zone of the heart and all of the two dimensional ultrasound frame data in the second set are acquired from the different, non-overlapping second spatial zone of the heart,
  wherein the frame data acquired from the first spatial zone and the frame data acquired from the second spatial zone for each of the first and second sets are acquired during a single cardiac cycle of the heart;
  organize the frame data acquired from the first spatial zone into a first temporal group;
  organize the frame data acquired from the second spatial zone into a second temporal group;
  spatially arrange the frame data in each of the first and second temporal groups frame data were acquired;
  combine the frame data in the first temporal group into a first three-dimensional imaged volume; and
  combine the frame data in the second temporal group into a second three-dimensional imaged volume.

16. The computer readable storage medium of claim 15, wherein the two dimensional ultrasound frame data includes image planes.

17. The computer readable storage medium of claim 15, wherein the imaged volume includes plural zones separated by a dividing plane and the instructions direct the STIC processor to sequentially acquire the first and second sets of the two dimensional ultrasound frame data on opposite sides of the dividing plane.

18. The computer readable storage medium of claim 17, wherein the imaged volume extends between opposite end planes with the dividing plane disposed therebetween, and the instructions direct the STIC processor to acquire the first and second sets of the two dimensional ultrasound frame data by proceeding in an outward progression from proximate to the dividing plane toward the end planes.

19. The computer readable storage medium of claim 17, wherein the imaged volume extends between opposite end planes with the dividing plane disposed therebetween, and the instructions direct the STIC processor to acquire the first and second sets of the two dimensional ultrasound frame data by obtaining the two dimensional ultrasound frame data by proceeding in an inward progression from proximate to the end planes toward the dividing plane.

* * * * *